US008128704B2

(12) United States Patent
Brown et al.

(10) Patent No.: US 8,128,704 B2
(45) Date of Patent: Mar. 6, 2012

(54) FEMORAL TROCHLEA PROSTHESES

(75) Inventors: Jeffrey D. Brown, Warsaw, IN (US);
Adam M. Griner, Columbia City, IN (US); Robert A. Hodorek, Warsaw, IN (US); Raymond C. Parisi, Wakarusa, IN (US); Brian E. Vanskyock, Fort Wayne, IN (US); Toby N. Farling, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 930 days.

(21) Appl. No.: 11/671,645

(22) Filed: Feb. 6, 2007

(65) Prior Publication Data

US 2008/0188855 A1  Aug. 7, 2008

(51) Int. Cl.
*A61F 2/38* (2006.01)
(52) U.S. Cl. ............ 623/20.15; 623/20.18; 623/20.19
(58) Field of Classification Search ........ 623/20.15, 623/20.18, 20.19
See application file for complete search history.

(56) References Cited

U.S. PATENT DOCUMENTS

| 5,336,266 | A | * | 8/1994 | Caspari et al. ............ 623/20.35 |
| 5,645,602 | A | * | 7/1997 | Albrektsson et al. ...... 623/23.11 |
| 5,702,459 | A | | 12/1997 | Hummer et al. |
| 5,879,354 | A | * | 3/1999 | Haines et al. .............. 606/86 R |
| 6,190,415 | B1 | | 2/2001 | Cooke et al. |
| 6,416,552 | B1 | * | 7/2002 | Hoeppner et al. ......... 623/20.15 |
| 6,616,696 | B1 | * | 9/2003 | Merchant .................. 623/20.18 |
| 6,797,006 | B2 | | 9/2004 | Hodorek |
| 2004/0236428 | A1 | | 11/2004 | Burkinshaw et al. |
| 2006/0122616 | A1 | * | 6/2006 | Bennett et al. ............. 606/87 |
| 2007/0123992 | A1 | | 5/2007 | Sanford |
| 2008/0188942 | A1 | | 8/2008 | Brown et al. |
| 2009/0281583 | A1 | | 11/2009 | Brown et al. |

FOREIGN PATENT DOCUMENTS

| FR | 2521421 A1 | 8/1983 |
| FR | 2594323 A1 | 8/1987 |
| FR | 2682589 A1 | 4/1993 |
| FR | 2740325 A1 | 4/1997 |
| WO | WO03/068119 A2 | 8/2003 |

OTHER PUBLICATIONS

The European Search Report mailed May 5, 2008, in related European application No. EP08250441.6.
The European Search REport maield May 27, 2008, in European application No. EP08250442.4.
Product Brochure, Natural-Knee II Patello-Femoral Joint System, Zimmer, Copyright 2005.

\* cited by examiner

*Primary Examiner* — Bruce E Snow
*Assistant Examiner* — Melissa Hoban
(74) *Attorney, Agent, or Firm* — Faegre Baker Daniels

(57) ABSTRACT

Various embodiments of femoral trochlea prostheses useable in a knee joint. The knee joint includes a patella and a distal femur with a femoral trochlea, or patello-femoral groove. In one embodiment, a femoral trochlea prosthesis includes a nonarticulating surface including contoured surfaces and/or planar surfaces. The present disclosure also provides a method for preparing a bone surface for receiving the prostheses described herein.

4 Claims, 9 Drawing Sheets

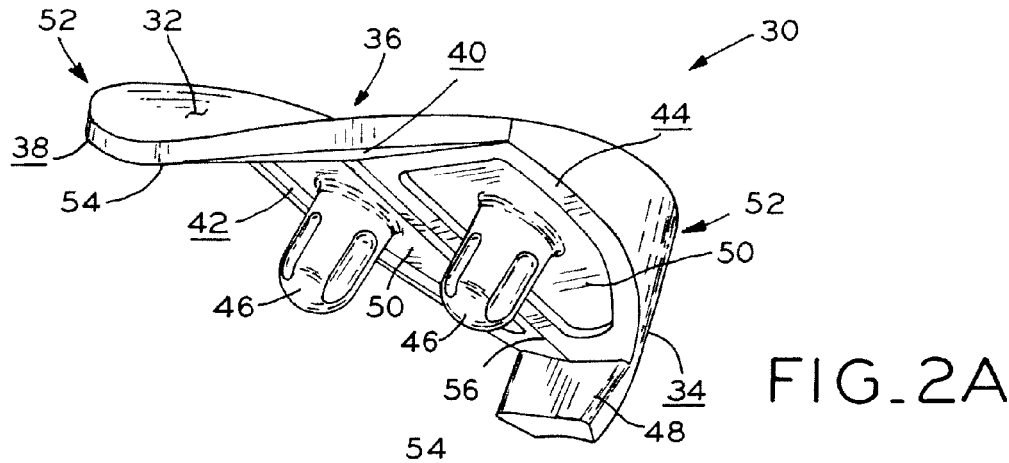
FIG_2A
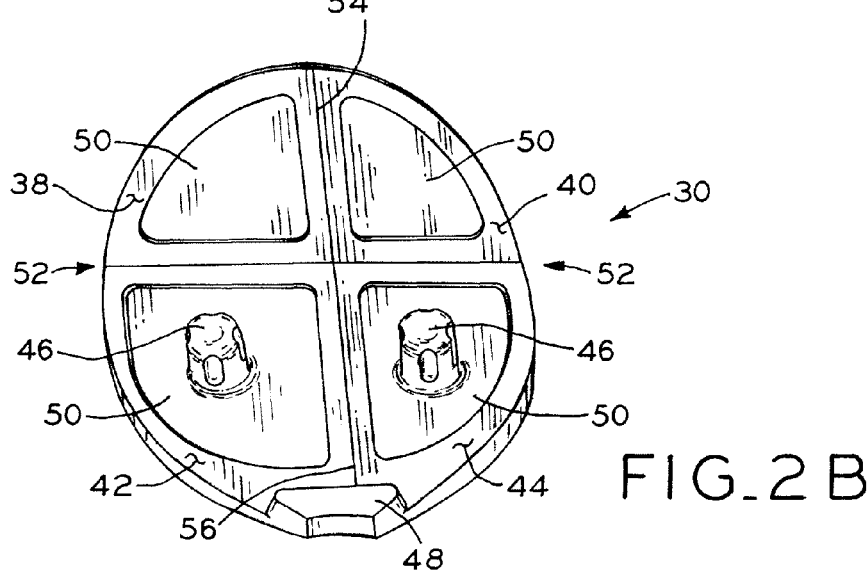
FIG_2B
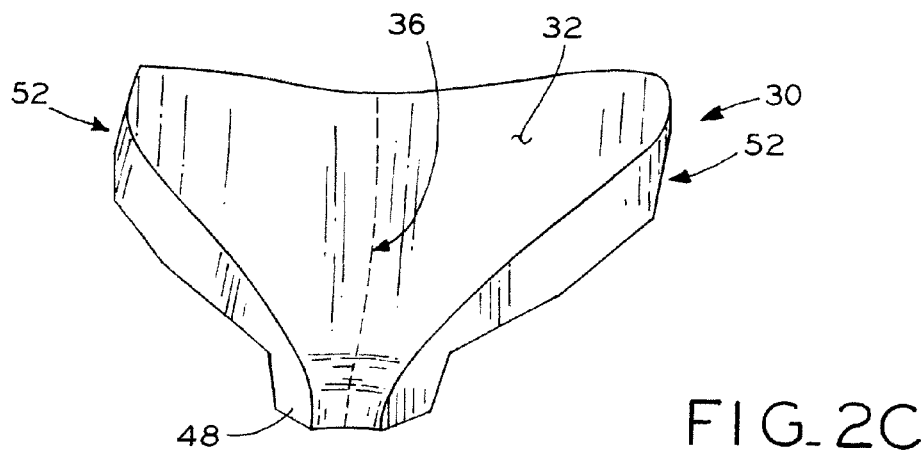
FIG_2C

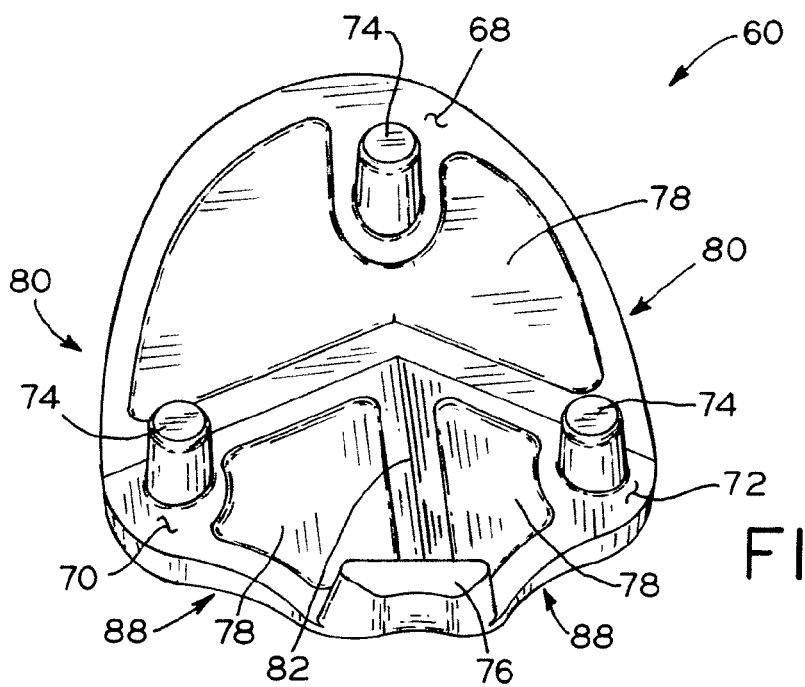
FIG_3A
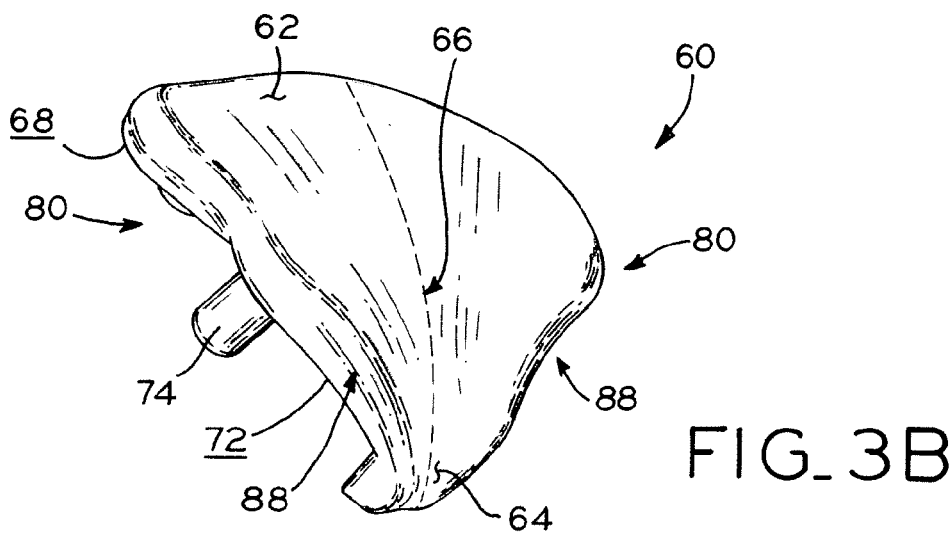
FIG_3B

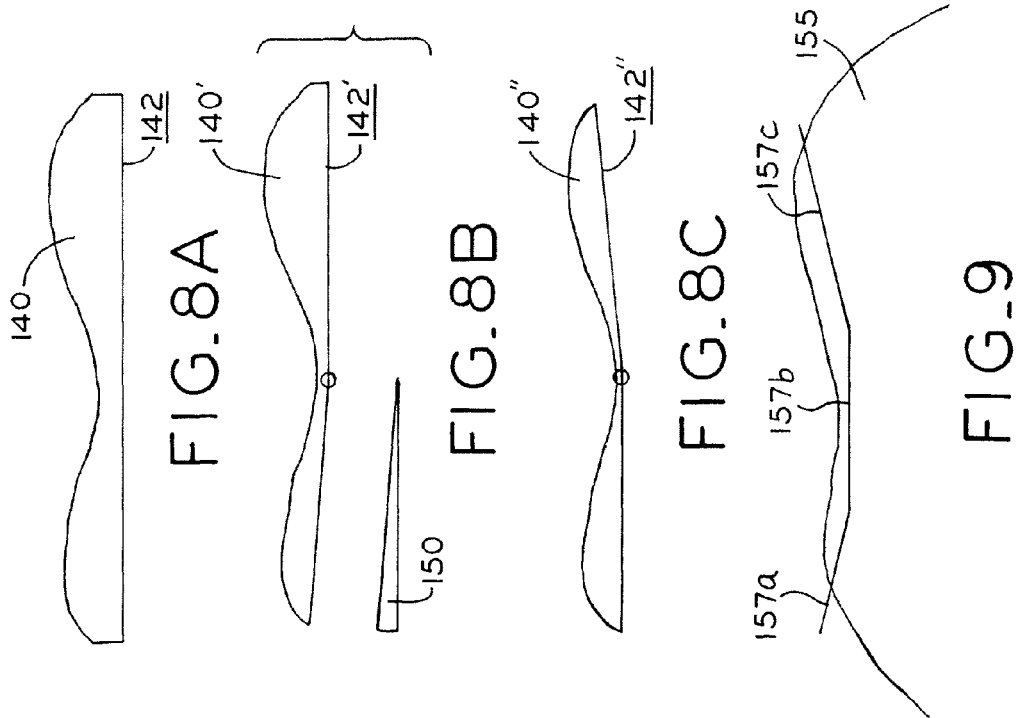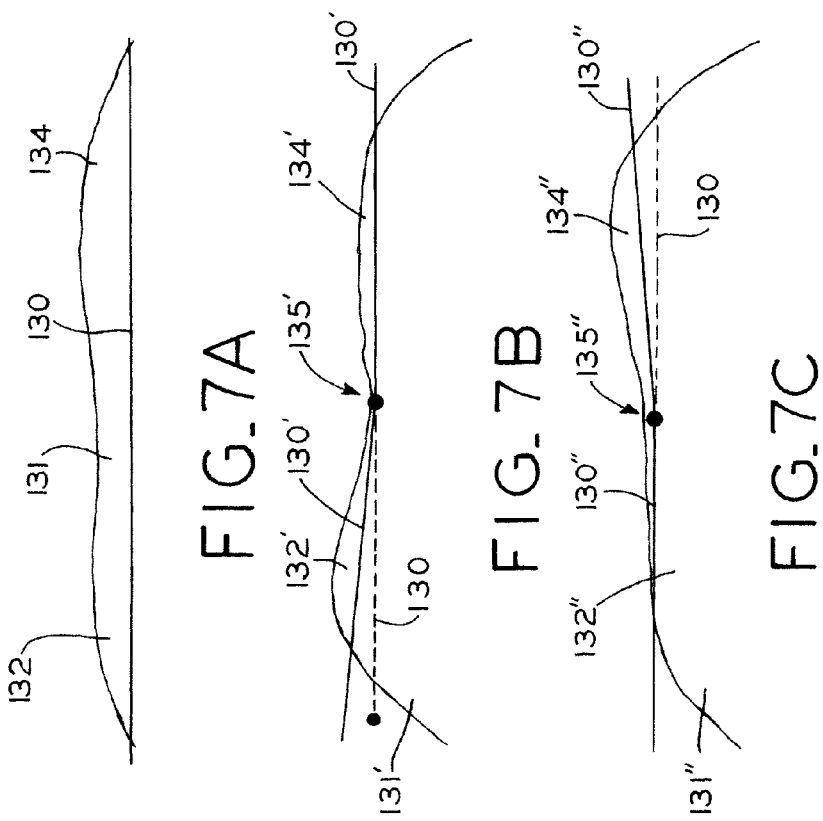

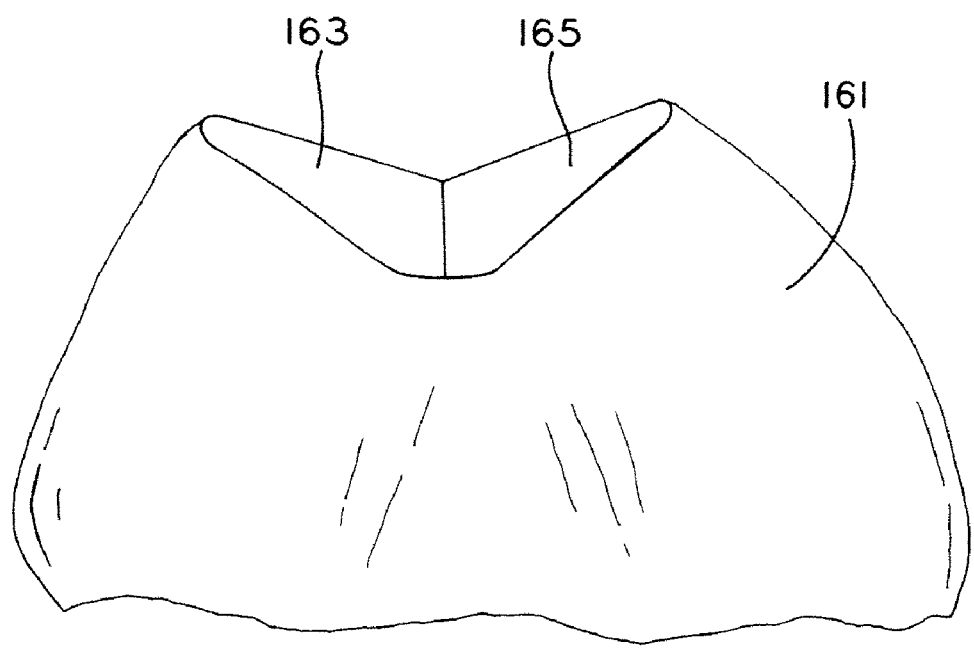
FIG_11

FEMORAL TROCHLEA PROSTHESES

BACKGROUND

1. Field of the Invention

The present invention relates to knee joint prostheses. More particularly, the present invention relates to various embodiments of exemplary femoral trochlea prostheses.

2. Description of the Related Art

Disease and trauma affecting the patello-femoral joint of a knee are commonly treated by surgically replacing the femoral trochlea with femoral trochlea implants or prostheses according to a procedure known as a patello-femoral joint (PFJ) replacement. Although femoral trochlea prostheses are provided in a range of varying sizes and are selected by surgeons to best fit the anatomy of a particular patient, improvements in the design of femoral trochlea prostheses are desired.

SUMMARY

The present disclosure provides various embodiments of femoral trochlea prostheses useable in a knee joint. The knee joint includes a patella and a distal femur with a femoral trochlea, or patello-femoral groove. In one embodiment, a femoral trochlea prosthesis includes a nonarticulating surface including contoured surfaces and/or planar surfaces. The present disclosure also provides a method for preparing a bone surface for receiving the prostheses described herein.

In one form thereof, the present disclosure provides a femoral trochlea prosthesis, including an articulating surface; a plurality of nonarticulating surfaces, the plurality of nonarticulating surfaces including at least one of: a first and a second planar distal nonarticulating surfaces, the first planar distal nonarticulating surface noncoplanar with the second planar distal nonarticulating surface; and a first and a second planar anterior nonarticulating surfaces, the first planar anterior nonarticulating surface noncoplanar with the second planar anterior nonarticulating surface.

In another form thereof, the present disclosure provides a femoral trochlea prosthesis, including an articulating surface; a plurality of nonarticulating surfaces, the plurality of nonarticulating surfaces including: a planar anterior nonarticulating surface; a first planar distal nonarticulating surface; and a second planar distal nonarticulating surface, the first planar distal nonarticulating surface noncoplanar with the second planar distal nonarticulating surface.

In yet another form thereof, the present disclosure provides a method for preparing an anatomical structure to receive a femoral trochlea prosthesis and for implanting the prosthesis in the anatomical structure, including the steps of resecting a portion of the anatomical structure by making one of a single planar resection along a line disposed at an angle with respect to a coronal plane of the anatomical structure; and at least a pair of planar resection lines, at least one of the pair of planar resection lines disposed at an angle with respect to a coronal plane of the anatomical structure; selecting a prosthesis to match the resection of the resecting step; and implanting the prosthesis with respect to the prepared anatomical structure.

In a still further form thereof, the present disclosure provides a method for preparing an anatomical structure to receive a femoral trochlea prosthesis and for implanting the prosthesis in the anatomical structure, including the steps of resecting a portion of the anatomical structure by making at least two noncoplanar cuts at a distal end of the anatomical structure, the two noncoplanar cuts defining a resected surface for a pair of distal nonarticulating surfaces of the prosthesis; selecting a femoral trochlea prosthesis to match the resection of the resecting step; and implanting the prosthesis with respect to the prepared anatomical structure.

BRIEF DESCRIPTION OF THE DRAWINGS

The above-mentioned and other features of this disclosure, and the manner of attaining them, will become more apparent and will be better understood by reference to the following description of embodiments of the disclosure taken in conjunction with the accompanying drawings, wherein:

FIG. 2A is a perspective view of an exemplary femoral trochlea prosthesis according to another embodiment of the present disclosure;

FIG. 2B is another perspective view of the prosthesis of FIG. 2A;

FIG. 2C is another perspective view of the prosthesis of FIG. 2A;

FIG. 3A is a perspective view of an exemplary femoral trochlea prosthesis according to yet another embodiment of the present disclosure;

FIG. 3B is another perspective view of the prosthesis of FIG. 3A;

FIG. 7A is a conceptual view of a resection line on a distal femur for preparing a bone to receive a femoral trochlea prosthesis;

FIG. 7B is a conceptual view of the resection line of FIG. 7A in comparison with a bone-preserving resection line according to another method of the present disclosure;

FIG. 7C is another conceptual view of the resection line of FIG. 7A in comparison with a bone-preserving resection line according to another method of the present disclosure;

FIG. 8A is a conceptual view of a femoral trochlea prosthesis used with the resection line of FIG. 7A;

FIG. 8B is a conceptual view of a femoral trochlea prosthesis used with the bone-preserving resection line of FIG. 7B;

FIG. 8C is a conceptual view of a femoral trochlea prosthesis used with the bone-preserving resection line of FIG. 7C;

FIG. 9 is a conceptual view of a bone-preserving resection line according to yet another method of the present disclosure;

FIG. 11 is a perspective view of a distal end of the femur, further illustrating a pair of distal planar resections.

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

The present disclosure provides various embodiments of femoral trochlea prostheses useable in a knee joint. The prostheses described herein may be useable in a knee joint in which a patella is resurfaces or a knee joint in which a patella is not resurfaced. The prostheses described herein may be secured to a femur with cement or, alternatively, without cement, such as with screws and/or cables, for example. The prostheses described herein may be formed of metal, polymer, or hydrogel. Moreover, due to the relatively small thicknesses of the prostheses described herein, the prostheses do not violate a primary total knee arthroplasty (TKA) envelope, i.e., minor or no adjustments of the primary TKA technique are required to revise a failed patello-femoral joint to a TKA.

Figure 1A:
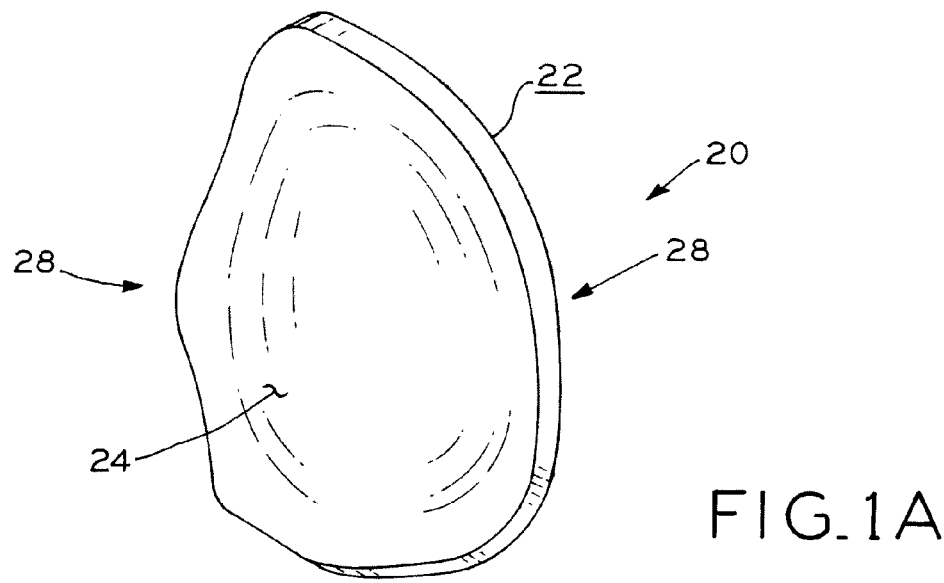
FIG. 1A is a perspective view of an exemplary femoral trochlea prosthesis according to one embodiment of the present disclosure.
Figure 1B:
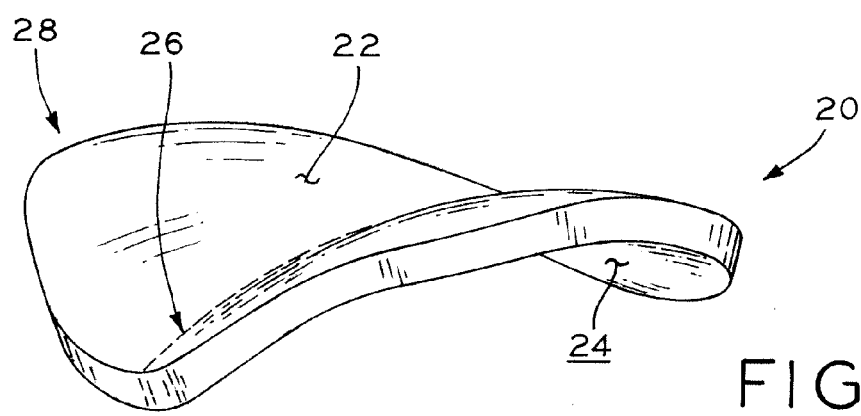
FIG. 1B is another perspective view of the prosthesis of FIG. 1A.
Figure 1C:
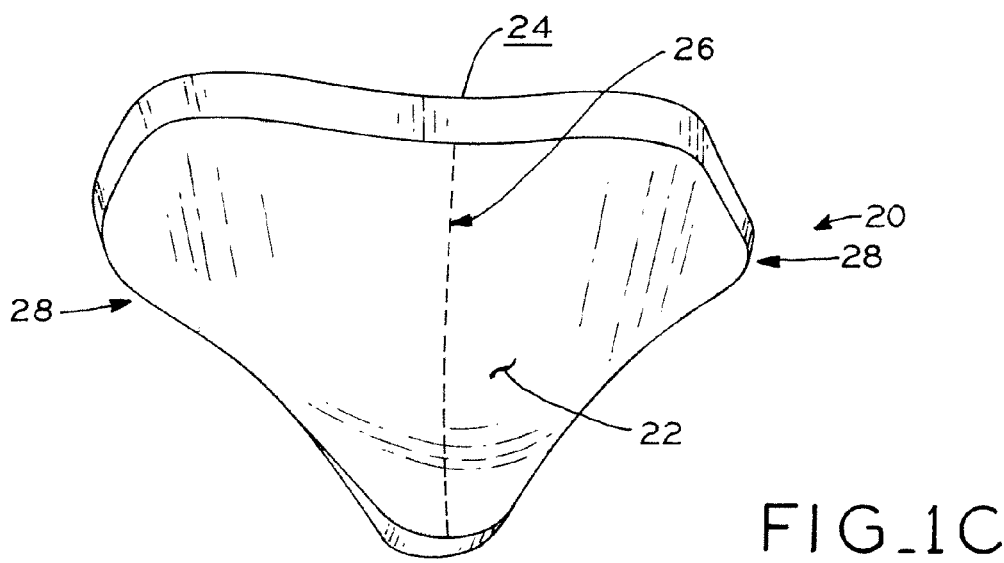
FIG. 1C is another perspective view of the prosthesis of FIG. 1A.

Referring to FIGS. 1A, 1B, and 1C, femoral trochlea prosthesis 20 may include articulating surface 22 and nonarticulating surface 24. Nonarticulating or bone-facing surface 24 may be contoured to have a substantially concave shape. Similarly, articulating surface 22 may include a convex portion, thereby defining trochlea groove 26 generally corresponding to the dashed lines of FIGS. 1B and 1C. Nonarticulating surface 24 also may include portions having a planar configuration. Prosthesis 20 may define a variable thickness between articulating surface 22 and nonarticulating surface 24. For example, prosthesis 20 may be thinnest near trochlea groove 26 and thickest near medial and lateral edges 28. Alternatively, the thickness of prosthesis 20 may be substantially uniform. Nonarticulating surface 24 of prosthesis 20 may include bone pegs and a distal tail substantially similar to those described in co-pending U.S. patent application Ser. No. 11/671,643 entitled FEMORAL TROCHLEA PROSTHESES, (hereinafter "the Co-Pending Application"), filed on the same day as the present application and assigned to the assignee of the present application, the disclosure of which is expressly incorporated herein by reference.

Referring to FIGS. 2A, 2B, and 2C, femoral trochlea prosthesis 30 may include a plurality of nonarticulating surfaces, anterior articulating surface or facet 32, and distal articulating surface or facet 34. Articulating surfaces 32 and 34 define patello-femoral groove 36 generally corresponding to the dashed line of FIG. 2C. Prosthesis 30 may include first anterior nonarticulating surface or facet 38, second anterior nonarticulating surface or facet 40, first distal nonarticulating surface or facet 42, and second distal nonarticulating surface or facet 44. In one embodiment, surfaces 38 and 42 are laterally positioned and surfaces 40 and 44 are medially positioned on prosthesis 30. In another embodiment, surfaces 38 and 42 are medially positioned and surfaces 40 and 44 are laterally positioned on prosthesis 30. Bone pegs 46 and distal tail 48 extending from distal nonarticulating surfaces 42, 44 may be substantially similar to the bone pegs and distal tails described in the Co-Pending Application which may be used to provide additional fixation support and strength for the femoral trochlea prostheses described herein. Nonarticulating surfaces 38, 40, 42, and 44 each may include pocket 50 which may be substantially similar to the pockets described in the Co-Pending Application which may be used to contain cement or porous material positioned between nonarticulating surfaces 38, 40, 42, 44 and the femur. Prosthesis 30 defines medial/lateral edges 52. Prosthesis 30 may define a variable thickness between nonarticulating surfaces 38, 40, 42, 44 and articulating surfaces 32, 34. In particular, in an exemplary embodiment, the thickness of prosthesis 30 decreases from one edge 52 inward toward groove 36 and then increases from groove 36 outward toward the other edge 52 to form groove 36 on articulating surfaces 32, 34.

First anterior nonarticulating surface 38 defines a first plane, second anterior nonarticulating surface 40 defines a second plane, first distal nonarticulating surface 42 defines a third plane, and second distal nonarticulating surface 44 defines a fourth plane. In an exemplary embodiment, the first, second, third, and fourth planes are not coplanar, i.e., each of the first, second, third, and fourth planes define unique planes which intersect each of the other three planes.

The intersection of the first plane and the second plane defines anterior apex 54. The intersection of the third plane and the fourth plane defines distal apex 56. Anterior apex 54 and distal apex 56 may closely follow the deepest part of sulcus or groove 36. Prosthesis 30 may be thinnest at anterior apex 54 and distal apex 56 as compared to the remainder of prosthesis 30 towards each edge 52 to facilitate the thinnest profile or thickness of prosthesis 30 along groove 36. Furthermore, the planar facets defined by nonarticulating surfaces 38, 40, 42, 44 remove the need to prepare a contoured surface on a distal femur to receive prosthesis 30.

Figure 3C:
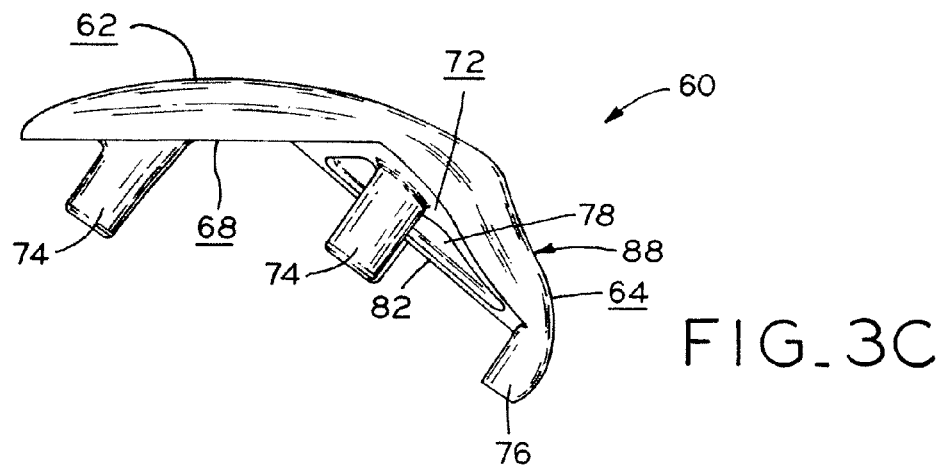
FIG. 3C is another perspective view of the prosthesis of FIG. 3A.

Referring to FIGS. 3A, 3B, and 3C, femoral trochlea prosthesis 60 may include a plurality of nonarticulating surfaces, anterior articulating surface 62, and distal articulating surface 64. Articulating surfaces 62 and 64 define patello-femoral groove 66 generally corresponding to the dashed line of FIG. 3B. Prosthesis 60 may include anterior nonarticulating surface 68, first distal nonarticulating surface 70, and second distal nonarticulating surface 72. Bone pegs 74 and distal tail 76 may be substantially similar to the bone pegs and distal tails described in the Co-Pending Application. Nonarticulating surfaces 68, 70, and 72 each may include pocket 78 which may be substantially similar to the pockets described in the Co-Pending Application. Prosthesis 60 defines medial/lateral edges 80. Prosthesis 60 defines a thickness between nonarticulating surfaces 68, 70, 72 and articulating surfaces 62, 64. In an exemplary embodiment, the thickness of prosthesis 60 decreases from one edge 80 inward toward groove 66 and then increases from groove 66 outward toward the other edge 80.

Anterior nonarticulating surface 68 defines a first plane, first distal nonarticulating surface 70 defines a second plane, and second distal nonarticulating surface 72 defines a third plane. In an exemplary embodiment, the first, second, and third planes are not coplanar, i.e., each of the first, second, and third planes define unique planes which intersect each of the other two planes.

The intersection of the second plane and the third plane defines distal apex 82. Distal apex 82 may closely follow the deepest part of groove 66. Prosthesis 60 is thinnest at distal apex 82 as compared to the remainder of prosthesis 60 to facilitate the thinnest profile or thickness of prosthesis 60 along groove 66. Furthermore, the planar facets defined by nonarticulating surfaces 68, 70, 72 remove the need to prepare a contoured surface on a distal femur to receive prosthesis 60.

Figure 3D:
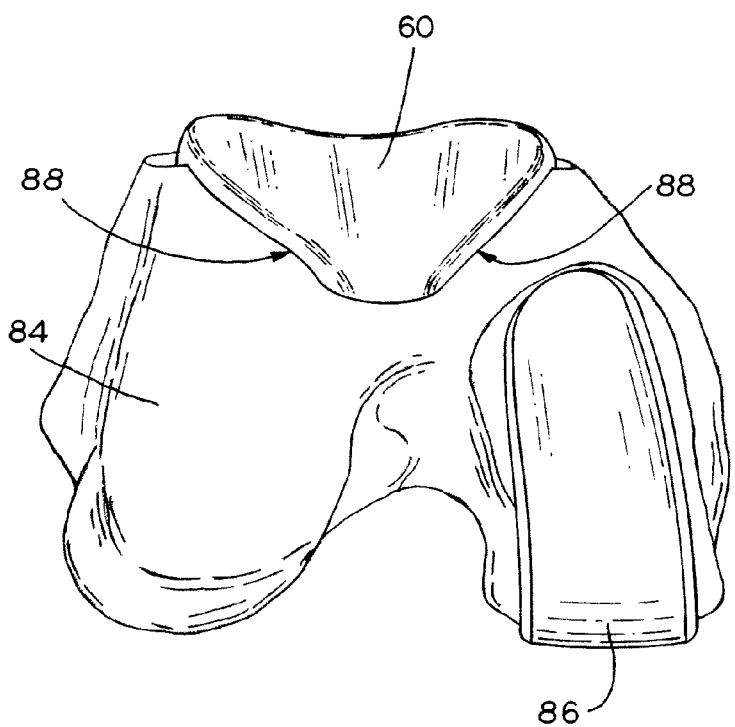
FIG. 3D is a perspective view of the prosthesis of FIG. 3A implanted in a distal femur, further illustrating a relationship between the prosthesis and a unicondylar knee prosthesis.

Referring now to FIG. 3D, femoral trochlea prosthesis 60 may be implanted on distal femur 84 proximate unicondylar knee prosthesis 86. Advantageously, prosthesis 60 may include distal cutouts 88 (FIGS. 3A-3D) such that prosthesis 60 is spaced from and does not contact prosthesis 86. Furthermore, cutouts or scallops 88 may eliminate interference with an anterior horn or portion of a meniscal component of the knee joint when the knee is in extension.

Figure 4A:
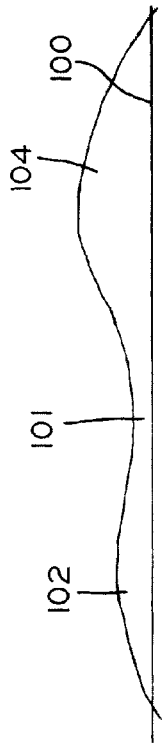
FIG. 4A is a conceptual view of a resection line on a distal femur for preparing a bone to receive a femoral trochlea prosthesis.
Figures 4B, 4C:
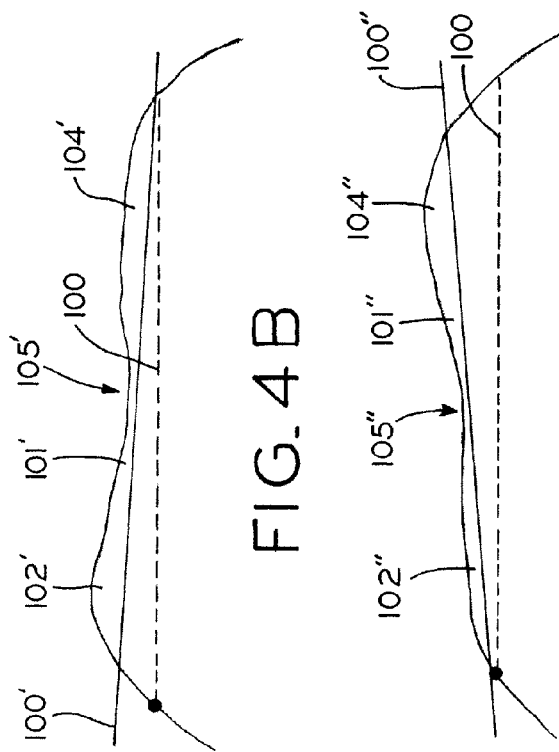
FIG. 4B is a conceptual view of the resection line of FIG. 4A in comparison with a bone-preserving resection line according to a method of the present disclosure.
FIG. 4C is another conceptual view of the resection line of FIG. 4A in comparison with a bone-preserving resection line according to a method of the present disclosure.

Referring now to FIGS. 4A, 4B, and 4C, bone-conserving resections are shown for a distal femur for receipt of any of the prostheses described herein and in the Co-Pending Application. As shown in FIG. 4A, distal femur 101 includes medial condyle 102 and lateral condyle 104. Resection line 100 represents a typical resection line for a normal distal femur 101. Distal femur 101 may not, however, always include normal anatomy. As shown in FIG. 4B, distal femur 101' includes medial condyle 102' and lateral condyle 104' which has a dysplastic condition, i.e., an abnormal anatomical condition in which lateral condyle 104' includes less bone stock as compared to a normal lateral condyle. Resection line 100 may satisfactorily accomplish the resection required for implantation of a femoral trochlea prosthesis on distal femur 101'. Resection line 100', however, may also accomplish the required resection while preserving bone. Similarly, as shown in FIG. 4C, distal femur 101" includes lateral condyle 104" and medial condyle 102" which has a dysplastic condition, i.e., an abnormal anatomical condition in which medial condyle 102" includes less bone stock as compared to a normal medial condyle. Resection line 100" may accomplish the required resection while preserving bone. Advantageously, resection lines 100' and 100" represent a surgical technique or method to cut a distal femur which accounts for variable anterior femoral anatomy while simultaneously preserving as much bone as possible. For example, resection line 100' extends medially/laterally across distal femur 101' as close as possible to patello-femoral groove 105' while also removing substantially equal amounts of bone from both medial condyle 102' and lateral condyle 104'. Similarly, resection line 100" extends medially/laterally across distal femur 101" as close as possible to patello-femoral groove 105" while also removing substantially equal amounts of bone from both medial condyle 102" and lateral condyle 104". This technique advantageously minimizes the bone removal and, consequently, preserves as much healthy bone as possible. In an alternative embodiment, a surgeon may choose to bias prostheses used with resection lines 100, 100', 100" to improve and/or restore patella subluxation resistance. For example, a 0° resection may be made to femur 101, but a 3° prosthesis may be used to bias one anterior condyle higher than the other condyle.

Figure 10:
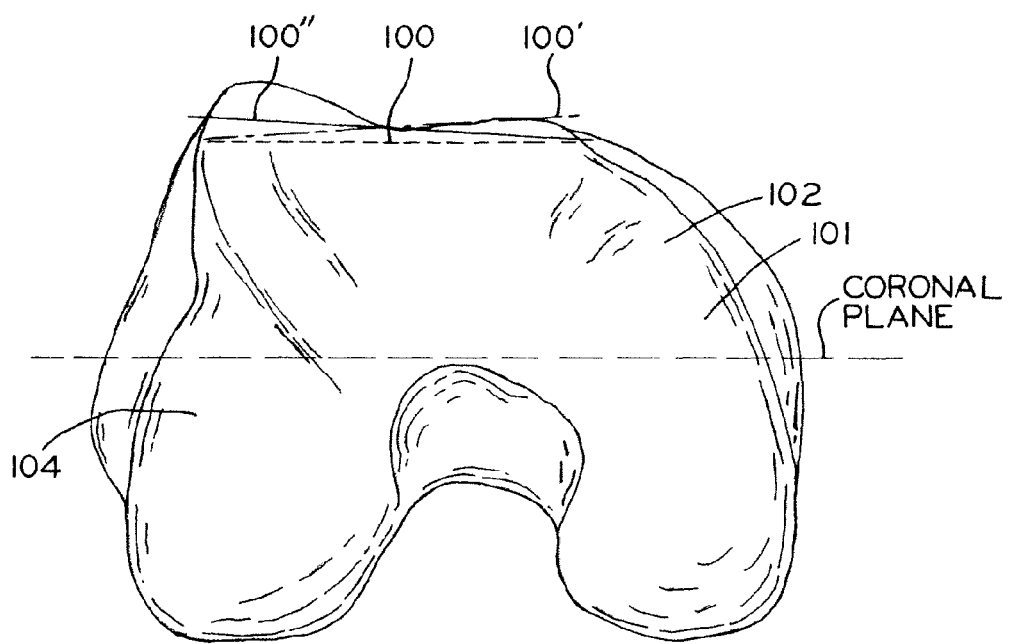
FIG. 10 is a distal perspective view of a distal end of the femur.

As shown in FIG. 10, resections lines 100, 100', and 100" are shown with respect to an inferior view of distal femur 101. Resection line 100 is substantially parallel to a coronal plane of femur 101. Resection lines 100' and 100" are disposed at an angle with respect to the coronal plane of femur 101.

Figure 5A:
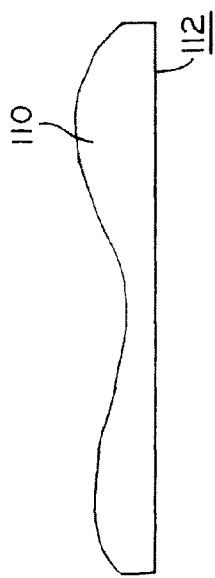
FIG. 5A is a conceptual view of a femoral trochlea prosthesis used with the resection line of FIG. 4A.
Figures 5B, 5C:
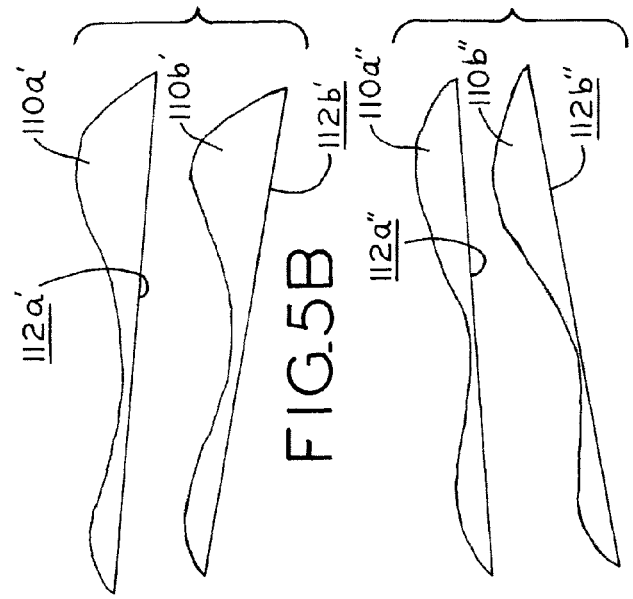
FIG. 5B is a conceptual view of a set of femoral trochlea prostheses used with the bone-preserving resection line of FIG. 4B.
FIG. 5C is a conceptual view of a set of femoral trochlea prostheses used with the bone-preserving resection line of FIG. 4C.

Referring to FIGS. 5A, 5B, and 5C, fragmentary profiles of femoral trochlea prostheses, such as those described above and in the Co-Pending Application, useable with the techniques described above with respect to FIGS. 4A, 4B, and 4C are shown. As shown in FIG. 5A, femoral trochlea prosthesis 110 including nonarticulating surface 112 may be used on distal femur 101 (FIG. 4A). Nonarticulating surface 112 abuts resection line 100 (FIG. 4A) on distal femur 101 when implanted on distal femur 101. As shown in FIG. 5B, femoral trochlea prostheses 110a' and 110b' including nonarticulating surfaces 112a' and 112b', respectively, may be used on distal femur 101' (FIG. 4B). Advantageously, nonarticulating surfaces 112a' and 112b' are angled with respect to surface 112 (FIG. 5A) to more closely match the prepared surface of distal femur 101' represented by resection line 100'. Prostheses 110a' and 110b' may include a thicker lateral condyle portion to account for the dysplastic condition and to more closely replicate normal anatomy when implanted on distal femur 101'. As shown in FIG. 5C, femoral trochlea prostheses 110a" and 110b" including nonarticulating surfaces 112a" and 112b", respectively, may be used on distal femur 101" (FIG. 4C). Advantageously, nonarticulating surfaces 112a" and 112b" are angled with respect to surface 112 (FIG. 5A) to more closely match the prepared surface of distal femur 101" represented by resection line 100". Prostheses 110a" and 110b" may include a thicker medial condyle portion to account for the dysplastic condition and to more closely replicate normal anatomy when implanted on distal femur 101". Advantageously, prostheses 110, 110a', 110b', 110a", and 110b" are also bone conserving due to the thin nature of the prostheses.

Figure 6A:
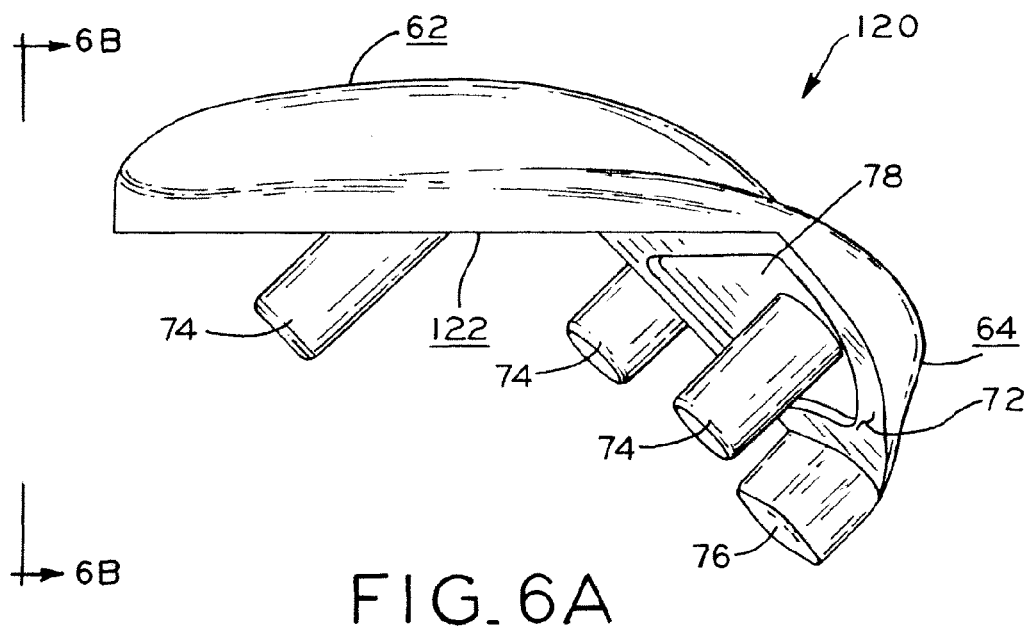
FIG. 6A is a perspective view of an exemplary femoral trochlea prosthesis according to a still further embodiment of the present disclosure.
Figure 6B:
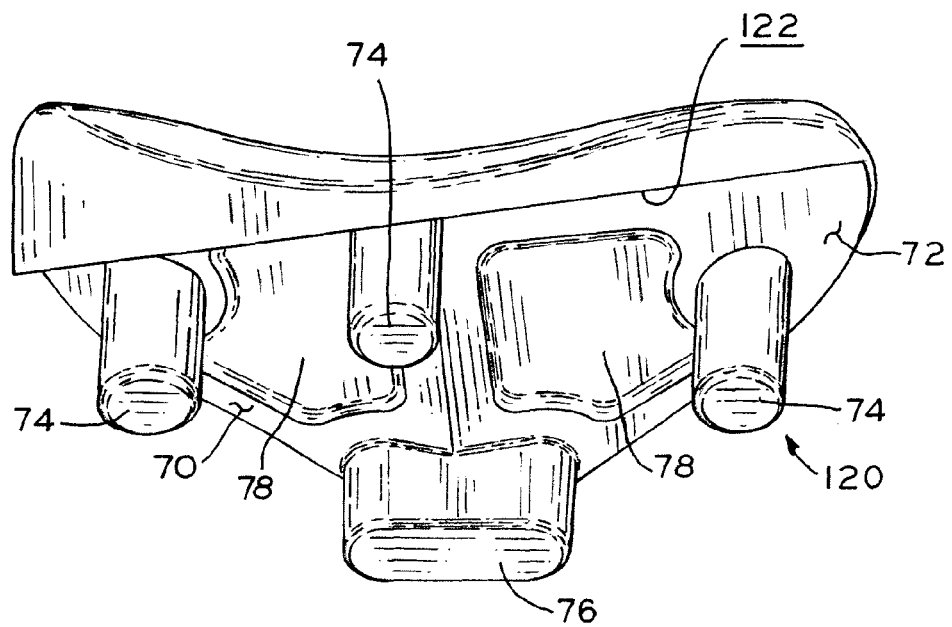
FIG. 6B is another perspective view of the prosthesis of FIG. 6A taken along line 6B-6B of FIG. 6A.

As shown in FIGS. 6A and 6B, femoral trochlea prosthesis 120 is shown which is substantially similar to prosthesis 60, described above with respect to FIGS. 3A-3D. Prosthesis 120 exemplifies the concepts illustrated in the fragmentary conceptual profiles of prostheses 110, 110a, and 110b, described above with respect to FIGS. 5A-5C. Femoral trochlea prosthesis 120 includes substantially the same components as prosthesis 60 except as described below. Anterior nonarticulating surface 122 of prosthesis 120 is angled as compared to anterior nonarticulating surface 68 (FIGS. 3A-3C). In this manner, anterior nonarticulating surface 122 may be configured to match the angle of resection lines 100' (FIG. 4B) or 100" (FIG. 4C), for example, while simultaneously replicating a normal anatomy of a distal femur on which prosthesis 120 is implanted.

Referring now to FIGS. 7A, 7B, and 7C, a bone-conserving resection is shown for a distal femur for receipt of any of the prostheses described herein and in the Co-Pending Application. As shown in FIG. 7A, distal femur 131 typically includes medial condyle 132 and lateral condyle 134. Resection line 130 represents a typical resection line for a normal distal femur 131. Distal femur 131 may not, however, always include normal anatomy. As shown in FIG. 7B, distal femur 131' includes medial condyle 132' and lateral condyle 134' which has a dysplastic condition, i.e., an abnormal anatomical condition. Resection line 130 may satisfactorily accomplish the resection required for implantation of a femoral trochlea prosthesis on distal femur 131'. Resection line 130', however, may also accomplish the required resection while preserving bone. In an exemplary embodiment, resection line 130' is formed as two noncolinear line segments, one of which extends as a beveled cut on the normal side of distal femur 131', i.e., medial condyle 132', and the other of which extends across the dysplastic side of distal femur 131', i.e., lateral condyle 134', which is substantially coincident with resection line 130. Similarly, as shown in FIG. 4C, distal femur 131" includes lateral condyle 134" and medial condyle 132" which has a dysplastic condition. Resection line 130" may accomplish the required resection while preserving bone. In an exemplary embodiment, resection line 130" is formed as two noncolinear line segments, one of which extends as a beveled cut on the normal side of distal femur 131", i.e., lateral condyle 134", and the other of which extends across the dysplastic side of distal femur 131", i.e., medial condyle 132", which is substantially coincident with resection line 130. Thus, resection lines 130' and 130" are formed by two planar cuts formed with an obtuse, oblique angle between the planes. A portion of resection lines 130' and 130" may substantially overlap or coincide with resection line 130, as shown in FIGS. 7B and 7C. Advantageously, resection lines 130' (FIG. 7B) and 130" (FIG. 7B) represent a surgical technique or method to cut a distal femur which accounts for variable anterior femoral anatomy while simultaneously preserving as much bone as possible. For example, resection line 130' extends medially/laterally across distal femur 131' as close as possible to patello-femoral groove 135' while also removing substantially equal amounts of bone from both medial condyle 132' and lateral condyle 134'. Similarly, resection line 130" extends medially/laterally across distal femur 132" as close as possible to patello-femoral groove 135" while also removing substantially equal amounts of bone from both medial condyle 132" and lateral condyle 134". This technique advantageously minimizes the bone removal and, consequently, preserves as much healthy bone as possible.

Referring to FIGS. 8A, 8B, and 8C, femoral trochlea prostheses useable with the techniques described above with respect to FIGS. 7A, 7B, and 7C are shown. As shown in FIG. 8A, femoral trochlea prosthesis 140 including nonarticulating surface 142 may be used on distal femur 131 (FIG. 7A). Nonarticulating surface 142 abuts resection line 130 (FIG. 7A) on distal femur 131 when implanted on distal femur 131. As shown in FIG. 8B, femoral trochlea prosthesis 140' including nonarticulating surface 142' may be used on distal femur 131' (FIG. 7B). Advantageously, nonarticulating surface 142' is beveled to more closely match the prepared surface of distal femur 131' represented by resection line 130'. Prosthesis 140' may include a thicker lateral condyle portion to account for the dysplastic condition and to more closely replicate normal anatomy when implanted on distal femur 131'. As shown in FIG. 8C, femoral trochlea prosthesis 140" including nonarticulating surface 142" may be used on distal femur 131" (FIG. 7C). Advantageously, nonarticulating surface 142" is beveled to more closely match the prepared surface of distal femur 131" represented by resection line 130". Prosthesis 140" may include a thicker medial condyle portion to account for the dysplastic condition and to more closely replicate normal anatomy when implanted on distal femur 131".

As shown in FIG. 8B, augment 150 may be used with any of the femoral trochlea prostheses described herein and in the Co-Pending Application to facilitate a more accurate fit with and orientation relative to a patient's anatomy and to more fully support a prosthesis when implanted. Augment 150 may have a generally triangular-shaped cross-section. Augment 150 may be formed of material such as, but not limited to, metal, polymethylmethacrylate (PMMA), polymer, a cobalt chromium alloy, or an open-cell porous metal such as a material made using Trabecular Metal™ technology, available from Zimmer, Inc. of Warsaw, Ind., for example. Augment 150 may placed proximate a medial condyle and/or a lateral condyle.

Referring to FIG. 9, distal femur 155 is shown. Distal femur 155 may include resection lines 157a, 157b, and 157c, similar to resection lines 100', 100", 130', 130", described above with reference to FIGS. 4B-4C and 7B-7C. Resection lines 157a, 157b, and 157c facilitate a bone-preserving bone resection surgical technique. In an exemplary embodiment, resection lines 157a, 157b, and 157c define unique planes. A plane defined by resection line 157a forms an oblique angle with a plane defined by resection line 157b. The plane defined by resection line 157b forms an oblique angle with a plane defined by resection line 157c. A surgical technique employing resection lines 157a, 157b, and 157c advantageously preserves bone while simultaneously prepares a surface of distal femur 155 to receive a femoral trochlea prosthesis. Any of the femoral trochlea prostheses described herein or in the Co-Pending Application may be used with a femur prepared with resection lines 157a, 157b, and 157c. A femoral trochlea prosthesis having at least five or six total facets on a nonarticulating surface thereof may be used with the surgical technique illustrated by resection lines 157a, 157b, and 157c. Advantageously, any prosthesis used with resection lines 157a, 157b, 157c may be dimensioned, for example, smaller than the cavity created by resection lines 157a, 157b, 157c, to permit subtle medial-lateral adjustment/movement of the prosthesis and to permit adjustment of the sulcus or trochlear groove angle of the prosthesis. Augment 150 (FIG. 8B) may be used with a prosthesis implanted after resection lines 157a, 157b, 157c are created. Augment 150 may be used proximate a medial condyle and/or a lateral condyle. Also, augment 150 may be used proximate resection line 157b, e.g., medially/laterally equidistant on distal femur 155.

FIG. 11 illustrates an exemplary resection for receipt of the distal nonarticulating surfaces described herein. For example, distal femur 161 may include planar cuts 163, 165 for receipt of distal nonarticulating surfaces 42, 44 (FIG. 2B) or 70, 72 (FIG. 3A).

All of the prostheses disclosed herein and in the Co-Pending Application may be specifically designed for gender specific applications. For example, the prostheses may be specifically designed for female anatomy and therefore include a greater lateral trochlear groove angle and a thinner anterior flange as compared to traditional prostheses. Further, for example, the prostheses may be specifically designed for male anatomy and therefore include a smaller lateral trochlear groove angle and a thicker anterior flange as compared to traditional prostheses.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A femoral trochlea prosthesis, comprising:
an articulating surface including a patello-femoral groove;
a plurality of nonarticulating surfaces, said plurality of nonarticulating surfaces including:
a planar anterior nonarticulating surface defining a plane extending between and including a medial edge of the prosthesis and a lateral edge of the prosthesis;
a first planar distal nonarticulating surface; and
a second planar distal nonarticulating surface,
said first planar distal nonarticulating surface noncoplanar with said second planar distal nonarticulating surface to form an intersection therebetween,
said first distal nonarticulating surface extending from the medial edge of the prosthesis toward said intersection with said second distal nonarticulating surface, said second distal nonarticulating surface extending from the lateral edge of the prosthesis toward said intersection with said first distal nonarticulating surface, said intersection forming a distal apex, said distal apex following said patello-femoral groove.

2. The femoral trochlea prosthesis of claim 1, wherein said planar anterior nonarticulating surface is noncoplanar with said first planar distal nonarticulating surface and said second planar distal nonarticulating surface.

3. The femoral trochlea prosthesis of claim 1, wherein said distal apex has a distal apex thickness defined between said distal apex and said patello-femoral groove of said articulating surface, one of said plurality of nonarticulating surfaces and said articulating surface defining a surface thickness spaced from said distal apex, said distal apex thickness less than said surface thickness.

4. The femoral trochlea prosthesis of claim 1, further comprising at least one scalloped region proximate said distal nonarticulating surfaces.

* * * * *